United States Patent [19]

Marciel

[11] Patent Number: Plant 7,558

[45] Date of Patent: Jun. 18, 1991

[54] MINIATURE POT ROSE NAMED DEVPRESA

[75] Inventor: Stanley G. Marciel, Aptos, Calif.

[73] Assignee: DeVor Nurseries, Inc., Watsonville, Calif.

[21] Appl. No.: 495,902

[22] Filed: Mar. 19, 1990

[51] Int. Cl.[5] ..... A01H 5/00

[52] U.S. Cl. ..... Plt./7

[58] Field of Search ..... Plt./7–9

*Primary Examiner*—James R. Feyrer

*Attorney, Agent, or Firm*—Charles W. Rummler

[57] ABSTRACT

A new and distinct miniature rose plant adapted for pot plant culture and particularly distinguished by its continuous and profuse production of relatively small, high center blooms of a generally Brick Red color on a free branching bush having a height of about 19 cm. growing in a 4 in. pot at an age of about 12 weeks, with a vigorous growth habit and abundant production of foliage comprising relatively small leaves.

1 Drawing Sheet

BACKGROUND OF THE NEW PLANT

This new variety of miniature pot rose originated as a seedling of a hybrid produced by me at Watsonville, Calif. by crossing the variety "Orange Sunblaze" (U.S. Plant Pat. No. 4,682) with pollen from an unnamed seedling selected from my collection of rose plants maintained for breeding purposes, this particular seedling having been selected for propagation because of the soft orange-red coloration of its blooms borne singly on strong upright stems of a plant having a general height of about 19 to 20 cm. and this was done by me at Watsonville by means of cuttings with such satisfactory results that such propagation was carried on through several successive generation at Watsonville which demonstrated conclusively that the novel characteristics of the parent plant would hold true from generation to generation and appeared to be firmly fixed.

DESCRIPTION OF THE DRAWING

This new rose plant is illustrated by the accompanying full color photographic drawing which shows a number of flowers in various stages of maturity and illustrates their form and character, the color rendition being as nearly true to that herein specified as is reasonably possible to obtain by conventional photographic procedures.

DESCRIPTION OF THE NEW VARIETY

The following is a detailed description of my new miniature rose plant based upon observation of greenhouse plants at Watsonville, Calif. with the color designations being according to The R.H.S. Colour Chart published by The Royal Horticultural Society of London, England.

THE PLANT

Origin: Seedling.

Parentage:

*Seed parent.*—Orange Sunblaze (U.S. Plant Pat. No. 4,682).

*Pollen parent.*—An unnamed and unpatented seedling.

Classification:

*Botanic.*—Hybrid miniature rose plant.

*Commercial.*—Miniature pot rose.

Form: An upright free branching bush.

Height: About 19 to 20 cm.

Growth: Vigorous, sturdy and upright.

Main stem length: About 138 mm. from the first flower cut.

*Color.*—Yellow-Green 146-B.

Branching character: Free branching.

Foliage:

*Quantity.*—Abundant.

*Size.*—Small.

*Number of leaves.*—6, from the last flower cut. Size: Average, about 67 mm. long.

*Leaflets.*—Number: 5. Size: About 27 mm. long and about 15 mm. wide. Shape: Ovate with denticulate margin. Texture: Leathery and smooth. Color: Upper side — Green 137-C. Under side — Greyed Green 191-A.

*Rachis.*—About 50 mm. for 7 part leaf.

*Petioles.*—About 10 mm. long.

Ribs and veins: Depressed on upper side and slightly rounded on the underside.

Thorns:

*Size.*—About 4 mm.

*Color.*—Greyed Red 182-D.

THE BUD

Size: Small.

*Diameter.*—About 17 mm.

*Length.*—About 18 mm.

Shape: Ovate.

Rate of opening: Slow.

Color of petals:

*When sepals first divide.*—Red 44-D.

*When petals begin to unfurl.*—Orange Red 35-B.

Sepals:

*Number* .—Five.

*Shape.*—Spreading with sparse small leafs protruding.

*Character.*—The sepals are hooded over the bud before dividing and they curl back when the flower opens.

*Color.*—Inside — Yellow Green 146-C. Outside — Yellow Green 144-A.

Calyx:

*Shape.*—Funnel-shaped.

*Size.*—Small.

*Splitting.*—Calyx does not split.

*Aspect.*—Smooth.

Peduncle:
*Length.*—About 50 mm.
*Character.*—Hairy, erect and slender.
*Color.*—Yellow Green 144-B.

THE FLOWER

Blooming habit: Continuous and profusely from early Spring through Winter, blooming freely under greenhouse conditions.
Size of bloom: Small in full bloom.
*Diameter.*—About 42 mm.
*Depth.*—About 15 mm.
Borne: Singly on strong generally upright stems.
Shape:
*When bloom first opens.*—Somewhat cup shaped with high center.
*When bloom matures.*—Slightly flattened.
Petalage:
*Number.*—28.
*Number of florets.*—4.
*Arrangement.*—Imbricated.
*Form.*—Ovate.
*Texture.*—Leathery.
*Appearance.*—Velvety.
*Color.*—Outer petals: Body — Orange Red 35-B. with Yellow Base 4-B. Inside petals: Body — Red 44-D.
Peduncle:
*Length.*—About 45 mm.
*Color.*—Yellow Green 144-B.
*Character.*—Sturdy and upright.
Discoloration after full bloom: Gradually turns to Red 49-A.

Persistence: The flowers hang on and dry.
Fragrance: Slight.
Disease resistance: Moderately resistant to mildew, rust and black spots as observed at Watsonville, Calif.
Lasting quality: Long lasting both on the plant and as a cut flower.

THE REPRODUCTIVE ORGANS

Stamens:
*Number.*—58.
*Arrangement.*—Slightly introrse.
*Anthers.*—Size: About 2 mm. Color: Yellow Orange 21-A.
*Filaments.*—Length: About 4 mm. Color: Yellow Orange 17-C.
*Pollen.*—Color: Yellow Orange 21-A.
Pistils:
*Number.*—25.
*Styles.*—Length: About 10 mm. Color: Yellow Green 145-C with tinges of Greyed Purple 186-B.
*Stigmas.*—Color: Yellow 4-D.
Character of the ovaries: Oval shaped and slightly flattened on one side.

I claim:

1. The new and distinct miniature pot rose, substantially as herein shown and described, characterized by its profuse and continuous production of very small flowers borne on strong stems growing from a 4 in. pot and having an average height of about 19 cm. and abundant foliage when grown to the age of about 12 weeks.

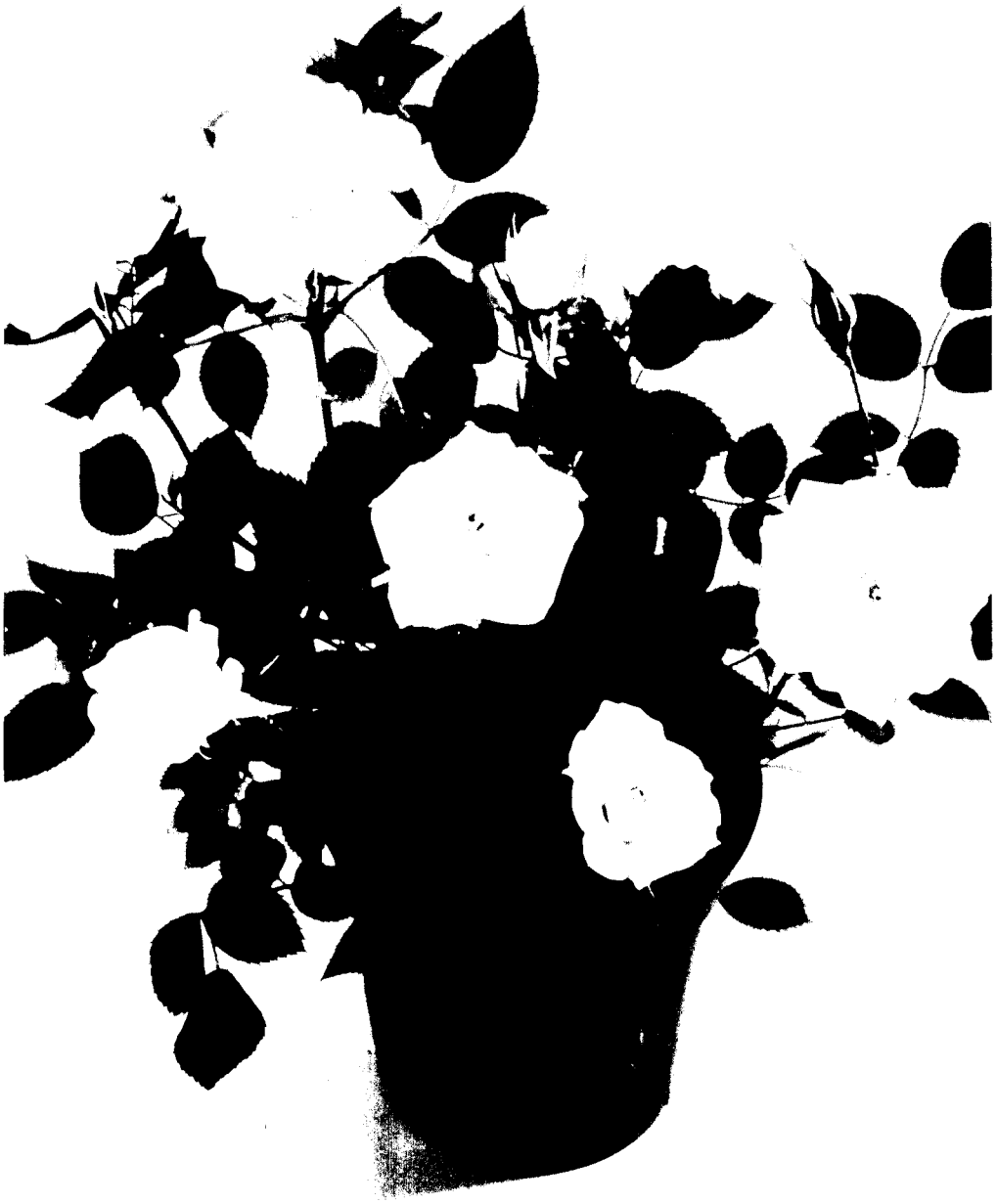

* * * * *